(12) United States Patent
Kobayashi et al.

(10) Patent No.: US 6,281,499 B1
(45) Date of Patent: Aug. 28, 2001

(54) METHOD FOR ANALYZING MEASURED VALUE BY ON-LINE SPECTRAL ANALYZER

(75) Inventors: Tomoyuki Kobayashi; Kouji Kobayashi; Kouichi Sato, all of Hachioji; Takeo Yamada, Yokohama, all of (JP)

(73) Assignee: Nireco Corporation, Tokyo (JP)

( * ) Notice: Subject to any disclaimer, the term of this patent is extended or adjusted under 35 U.S.C. 154(b) by 0 days.

(21) Appl. No.: 09/300,849

(22) Filed: Apr. 28, 1999

(30) Foreign Application Priority Data

May 12, 1998 (JP) .................................................. 10-128566

(51) Int. Cl.⁷ ..................................................... G01N 21/35
(52) U.S. Cl. ........................................ 250/339.09; 702/85
(58) Field of Search ......................... 250/339.09; 702/85

(56) References Cited

U.S. PATENT DOCUMENTS 5,933,792 * 8/1999 Andersen et al. ..................... 702/32

\* cited by examiner

*Primary Examiner*—Constantine Hannaher
(74) *Attorney, Agent, or Firm*—McDermott, Will & Emery

(57) ABSTRACT

An object to be measured is analyzed by a chemical means or a physical means to make its characteristic value clear, a spectrum of the same object to be measured is obtained by an off-line near infrared spectral analyzer, a calibration indicative of a relation between the spectrum and the characteristic value is obtained, at least one sample is selected from among the same kind of objects to be measured, spectra are obtained by the off-line near infrared spectral analyzer and an on-line near infrared spectral analyzer, a difference between both of the obtained spectra is obtained, a spectrum of the same kind of object to be measured is measured by the on-line near infrared spectral analyzer, the measured spectrum is corrected by the difference between both of the spectra, and the characteristic value of the object to be measured is estimated by using the corrected spectrum and the calibration.

5 Claims, 5 Drawing Sheets

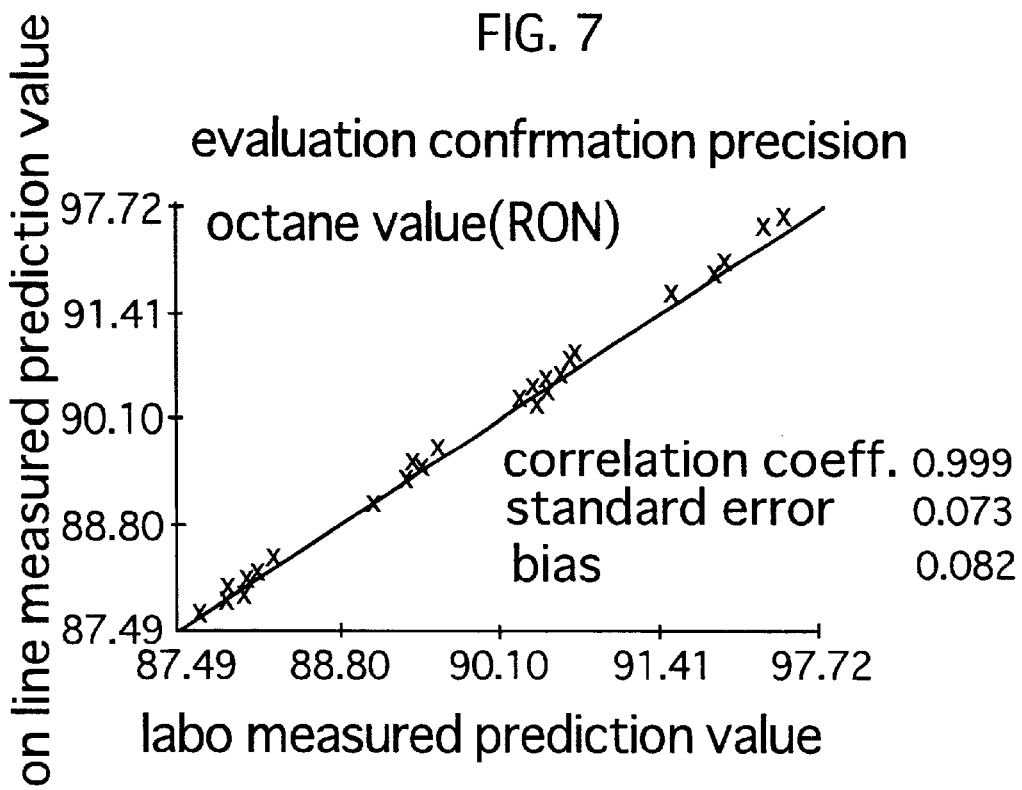
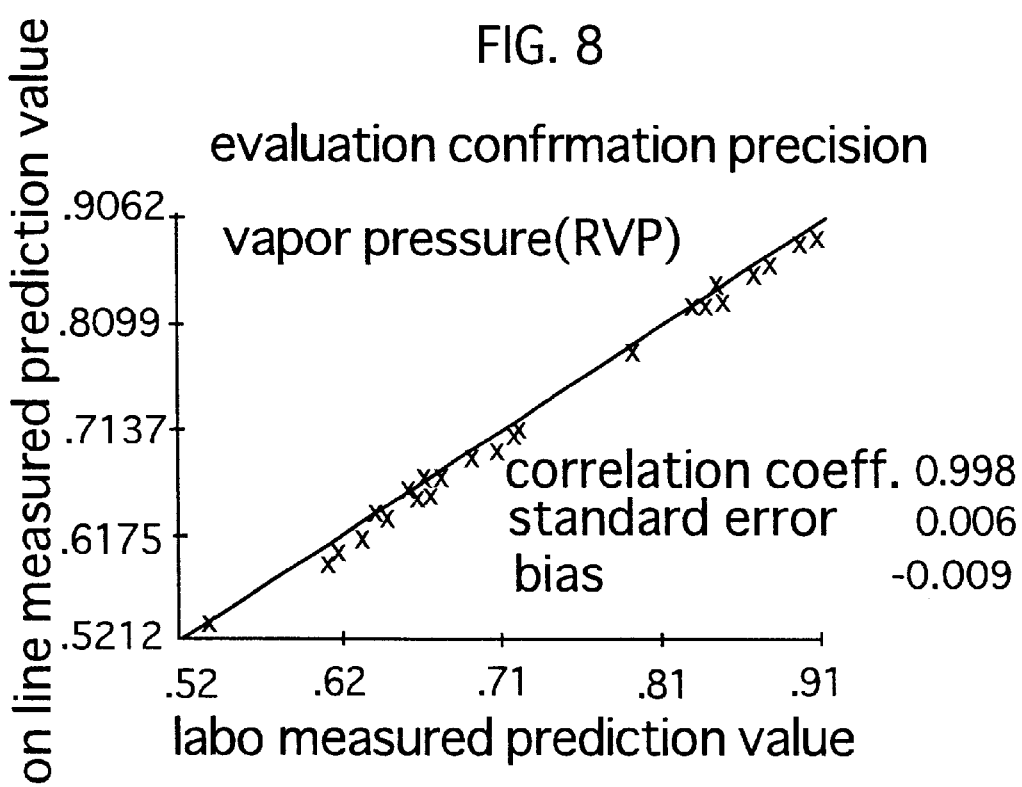

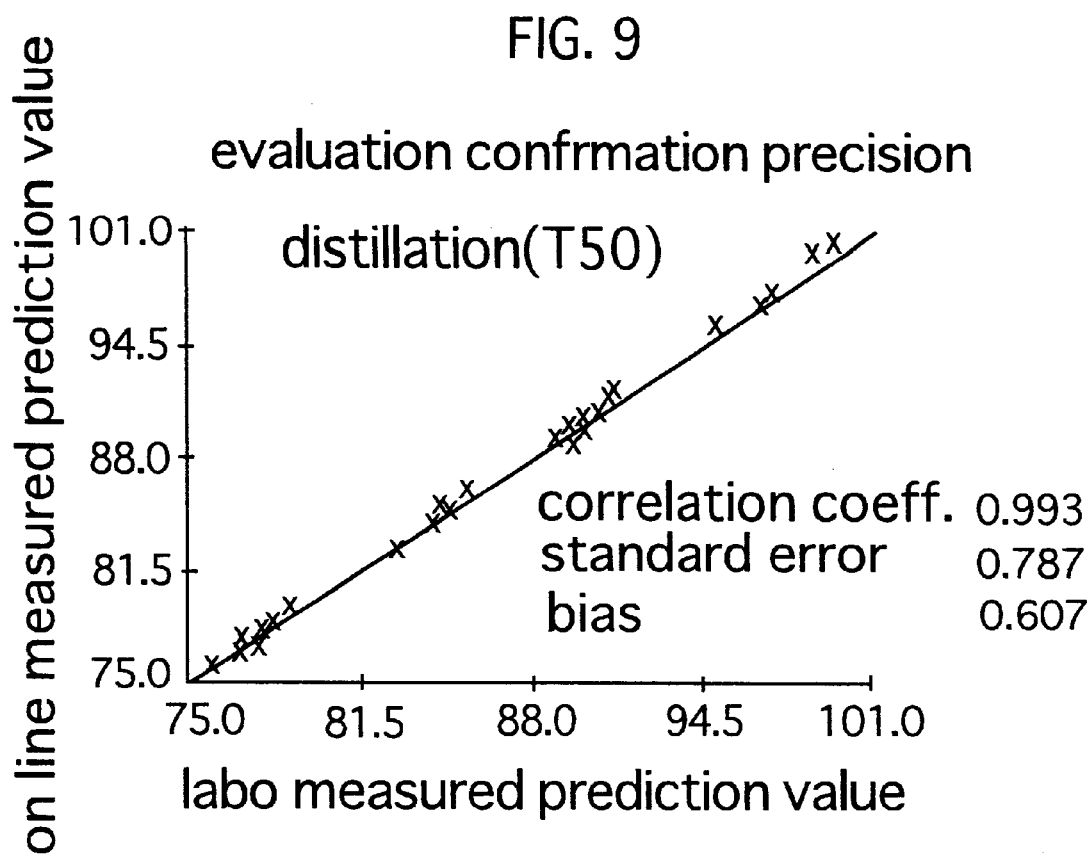

METHOD FOR ANALYZING MEASURED VALUE BY ON-LINE SPECTRAL ANALYZER

BACKGROUND OF THE INVENTION (i) Field of the Invention

The present invention relates to a method for analyzing data by an on-line near infrared spectral analyzer.

(ii) Description of the Related Art

As a manufacturing process management, there are an off-line management and an on-line management. In the off-line management, a specimen sampled from a manufacturing line is sent to an analyzing room which is away from the line, its characteristic value is analyzed, and the result is fed back to the line. In the analysis, a chemical analysis is performed in many cases, so that it takes a long time for the analysis. In the on-line management, a specimen sampled by an automatic sampler is automatically sent to an analytical instrument and is automatically analyzed. An analytical result is fed back to the line.

In recent years, a technique for a non-destructive inspection using a near infrared spectroscopy has progressed and is used to analyze protein or starch of food or feed. Consequently, time and costs are sharply reduced as compared with a conventional chemical analysis. As for an object to be measured as well, not only chemical characteristics but also physical characteristics can be measured. Although the near infrared spectroscopy or an infrared spectroscopy is used in the on-line analysis in few cases so far, as effects of a laboratory analysis become more apparent, needs of the on-line analysis are being raised.

In the near infrared spectroscopy, an object to be measured is analyzed by a chemical means or a physical means to make its characteristic value clear, a spectrum of the same object to be measured is obtained by a laboratory near infrared spectral analyzer, and a calibration indicative of a relation between the spectrum and the characteristic value is formed. The spectrum of the next target to be measured is measured by the laboratory near infrared spectral analyzer and the characteristic value of the object to be measured is estimated from the spectrum and the calibration. In order to form the calibration, works such as chemical analysis and clarification of physical characteristics of a large quantity of objects to be measured are needed.

When the on-line analysis is performed by the near infrared spectroscopy, the calibration formed by the laboratory near infrared spectral analyzer cannot be used as it is. Hitherto, since the structure of the spectral analyzer is complicated, even in case of the spectral analyzers having the same structure, the sampling measurement is performed by each spectral analyzer and the calibration is obtained by each spectral analyzer. Particularly, an optical fiber is used in a near infrared spectral analyzer for on-line in many cases. Since the optical fiber is not used in the near infrared spectral analyzer for laboratory (for off-line) in most of cases, however, a difference in spectral characteristics occurs. In an optical system using a diffraction grating for laboratory, dispersed light is irradiated onto an object. However, in the system for on-line, white light is irradiated onto a sample and there is a case where transmission light or reflection light is dispersed by the diffraction grating. It is impossible to transfer or share the calibration between the spectral analyzers having different structures as mentioned above, so that it is considered that the on-line analysis is difficult.

SUMMARY OF THE INVENTION

The present invention is made in consideration of the above-mentioned problems and it is an object to provide a method for analyzing a measured value by an on-line spectral analyzer in which a calibration for off-line can also be used for on-line.

The invention provides a method for analyzing an object to be measured, by a chemical means or a physical means to make its characteristic value clear, obtaining a spectrum of the same object to be measured, by an off-line near infrared spectral analyzer, obtaining a calibration indicative of a relation between the spectrum and the characteristic value, selecting at least one sample from among the same kind of objects to be measured, obtaining spectra by the off-line near infrared spectral analyzer and an on-line near infrared spectral analyzer, obtaining a difference between both the obtained spectra, measuring a spectrum of the same kind of object to be measured, by the on-line near infrared spectral analyzer, correcting the measured spectrum by the difference between both the spectra, and estimating a characteristic value of the object to be measured, by using the corrected spectrum and the calibration.

In a preferred embodiment, as above-mentioned one sample, a sample showing a substantially central value in a measurement range which is covered by the calibration is used.

In another preferred embodiment, when the object to be measured is changed and an estimated error of the characteristic value exceeds an allowable value in the calibration, a sample of the object to be measured is added and is measured by the off-line infrared spectral analyzer, the calibration is corrected, the corrected calibration is transferred to the on-line spectral analyzer, and the characteristic value of the object to be measured is estimated.

In another preferred embodiment, spectra of the same object to be measured are obtained by the on-line near infrared spectral analyzer and the off-line near infrared spectral analyzer, a difference between both of newly obtained spectra is compared with the difference between both the spectra obtained already and, when the difference between the new spectra is larger, the characteristic value of the object to be measured is estimated by using the difference between the new spectra.

In another preferred embodiment, the calibration obtained by the off-line near infrared spectral analyzer is used by a plurality of on-line near infrared spectral analyzers.

The advantages obtained by the aforementioned present invention will be described hereinbelow.

At least one sample is selected from among the same kind of objects to be measured, the sample is analyzed by the off-line near infrared spectral analyzer and the on-line near infrared spectral analyzer to obtain spectra, and a difference between both the obtained spectra is obtained. Subsequently, a spectrum of the same kind of object to be measured is measured by the on-line near infrared spectral analyzer and the difference between both the spectra is added to or subtracted from the measured spectrum, whereby measurement data of the on-line near infrared spectral analyzer is converted into data of the off-line near infrared spectral analyzer. Consequently, the characteristic value of the object to be measured can be estimated on the basis of the data converted by using the calibration of the off-line near infrared spectral analyzer.

Although the calibration is formed on the basis of a chemical analysis or a physical analysis for a large number of samples, the difference between both the spectra is obtained by using such a sample having a value that is located at a substantially center position of the measurement range at which the calibration is effective. Consequently, a precision of the difference between both the spectra is raised.

There is a case where the characteristic value of the object to be measured serving as a target to be measured is changed. In this case, a sample of the object to be measured is added and is measured by the off-line infrared spectral analyzer and the calibration is corrected, so that the measurement capable of coping with the change in characteristic value of the object to be measured can be performed.

An aging change of the on-line near infrared spectral analyzer appears as a change in spectrum. After an elapse of predetermined using time, the same object to be measured is measured by the on-line and off-line near infrared spectral analyzers to obtain spectra. When a difference between both the spectra is different from the difference which has already been obtained, the characteristic value of the object to be measured is obtained on the basis of the new difference between the spectra, so that the aging change can be corrected.

When the calibration obtained by one off-line near infrared spectral analyzer is used in a plurality of on-line near infrared spectral analyzers, there is no obstacle and an economical merit is large.

As will be obviously understood from the above description, according to the invention, the calibration formed by the laboratory analyzer can be easily transferred to the on-line analyzer and the on-line analysis can be performed, so that it can contribute largely to an improvement in yield of industrial products. As for a periodic maintenance of the on-line analyzer as well, there is provided a method of realizing the maintenance by on-line as it is. Since one laboratory analyzer can be applied to a lot of on-line analyzers, an economic system can be provided.

The above and other objects and advantageous features of the present invention will be made apparent from the following description made with reference to the accompanying drawings, in which like reference characters designate the same or similar parts throughout the drawings.

BRIEF DESCRIPTION OF THE DRAWINGS

FIG. 7 is a correlation diagram between a measured prediction value of the laboratory analyzer and a measured prediction value of the on-line analyzer with respect to an octane value of gasoline;

FIG. 8 is a correlation diagram between a measured prediction value of the laboratory analyzer and a measured prediction value of the on-line analyzer with respect to a vapor pressure of gasoline; and FIG. 9 is a correlation diagram between a measured prediction value of the laboratory analyzer and a measured prediction value of the on-line analyzer with respect to distillation of gasoline.

DETAILED DESCRIPTION OF THE PREFERRED EMBODIMENTS

Figure 1:
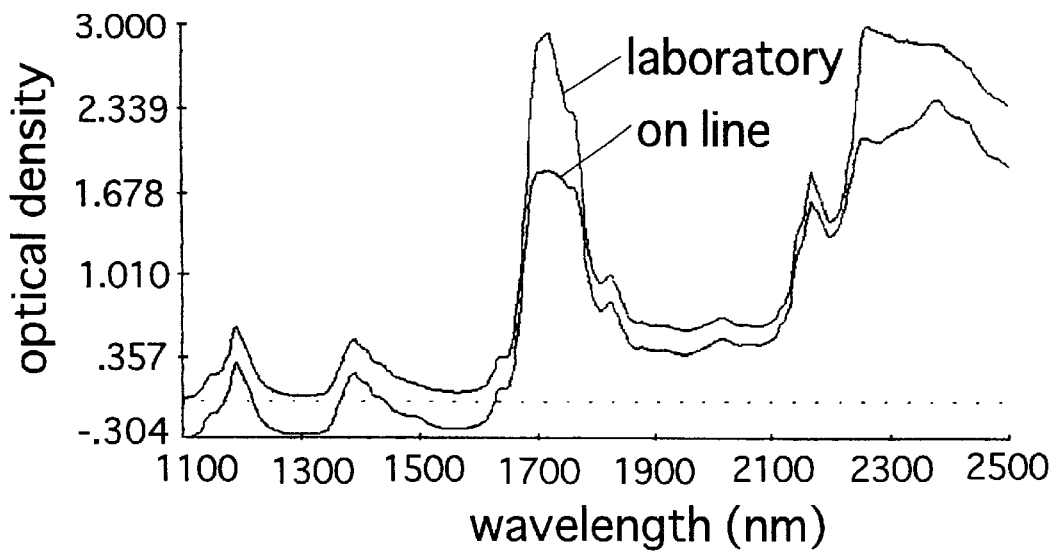
FIG. 1 shows spectra obtained by measuring the same gasoline sample by a laboratory analyzer and an on-line analyzer.

Embodiments of the present invention will now be explained hereinbelow with reference to the drawings.

An on-line near infrared spectral analyzer is called an on-line analyzer, an off-line near infrared spectral analyzer is called a laboratory analyzer, and a chemically analyzed value or a measured value by a physical means is called a hand analyzed value or a laboratory value. Specifications of the used analyzers are shown as follows.

Laboratory analyzer

Liquid System S/N 2120, Transmittance Mode Auto-Gain Cuvette Cell 10.0 mm, Wavelength range 1100 to 2500 nm On-line analyzer Online 5000 S/N 2986, Transmittance Mode Non-Auto-Gain Fiber Probe 5.0 mm (10.0 mm), Wavelength range 1100 to 2500 nm Estimation of a characteristic value of an object by the near infrared spectroscopy is performed to a manufacturing line of liquid or a solid or granular material in a petrochemical field. In the present embodiment, a method for measuring and analyzing a characteristic value of gasoline by the on-line analyzer will be explained. For gasoline, items such as an octane value (RON), a vapor pressure (RVP), or distillation (for instance, it is shown as T50 at a temperature at which 50% of gasoline is evaporated) are measured in an on-line manner.

Measurement and analysis of the characteristic value of gasoline by the on-line analyzer are performed by the following three steps.

First Step

Samples of objects to be measured are prepared and the characteristic values RON, RVP, and T50 are measured (the measured values are called hand analyzed values or laboratory values) by the chemical analysis or physical means. Simultaneously, a spectrum of each sample is measured by using the laboratory analyzer. Calibrations indicative of the relations between the spectra and the above-mentioned characteristic values are formed by a statistical practice. The calibration is formed every characteristic value, namely, RON, RVP, and T50. Since a composition of gasoline differs due to a producing district of crude oil and a productive distribution of a refining line changes due to a season, a change in base material of gasoline is large, so that a period to collect samples is long. It is known that in case of the long period, one year is required to form the calibrations in one refinery. Hitherto, when the refinery differs, the calibration cannot be used in common, so that it is formed every refinery.

Second step

In order to transfer the calibration formed by the laboratory analyzer to the on-line analyzer, the following work is performed. One sample is selected from among objects to be measured, spectra are obtained by the laboratory analyzer and on-line analyzer, and a difference between the two obtained spectra (for example, a difference obtained by subtracting the spectrum of the on-line analyzer from that of the laboratory analyzer) is obtained. The difference denotes a meter difference of the two spectral analyzers. On the basis of the measurements of many samples, the present inventor has found such a fact that when the objects to be measured are the same kind (for example, in case of gasoline, even when the producing district differs), the meter difference is substantially constant. He has also found such a fact that when the meter difference is calculated by one sample, there is no problem. The present invention is based on such discoveries. As one sample, if possible, it is preferable that a sample having a value near the center of the measurement range is selected. For instance, in case of measuring the octane value RON of gasoline, when the measurement range is equal to 85 to 94, a sample of about 90 is selected. However, when the items to be measured are three items like the case of gasoline (RON, RVP, and T50), it is not guaranteed that the sample has a value that is close to the center value for each item. Therefore, when it is measured with respect to a plurality of items as mentioned above, a sample having a value near the center value for the item which is regarded as important, for example, for the measurement range of RON is selected.

Third step

The meter difference and the calibration formed by the laboratory analyzer are stored into the on-line analyzer. In the on-line analyzer, the spectrum obtained by measuring the object to be measured in an on-line manner is corrected by the meter difference. That is, the meter difference is added to the spectrum of the on-line analyzer. (When the meter difference is obtained by subtracting the spectrum of the laboratory analyzer from that of the on-line analyzer, the meter difference is subtracted from the spectrum of the on-line analyzer.) Consequently, the spectrum of the on-line analyzer is converted into that of the laboratory analyzer. The added spectrum is analyzed by using the calibration formed by the laboratory analyzer, thereby obtaining a predicted value of the item to be measured. The above analysis is performed by a computer and the result is displayed on a monitor screen.

An example of data obtained in the above steps will now be described.

FIG. 1 shows spectra obtained by measuring the same sample by the laboratory analyzer and on-line analyzer. An axis of abscissa denotes a wavelength (nm) and an axis of ordinate indicates an optical density (log(1T), T denotes a transmission index). The same shall also apply to FIGS. 2 and 3. A sample is regular gasoline. A laboratory analyzed value is larger than an on-line analyzed value.

Figure 2:
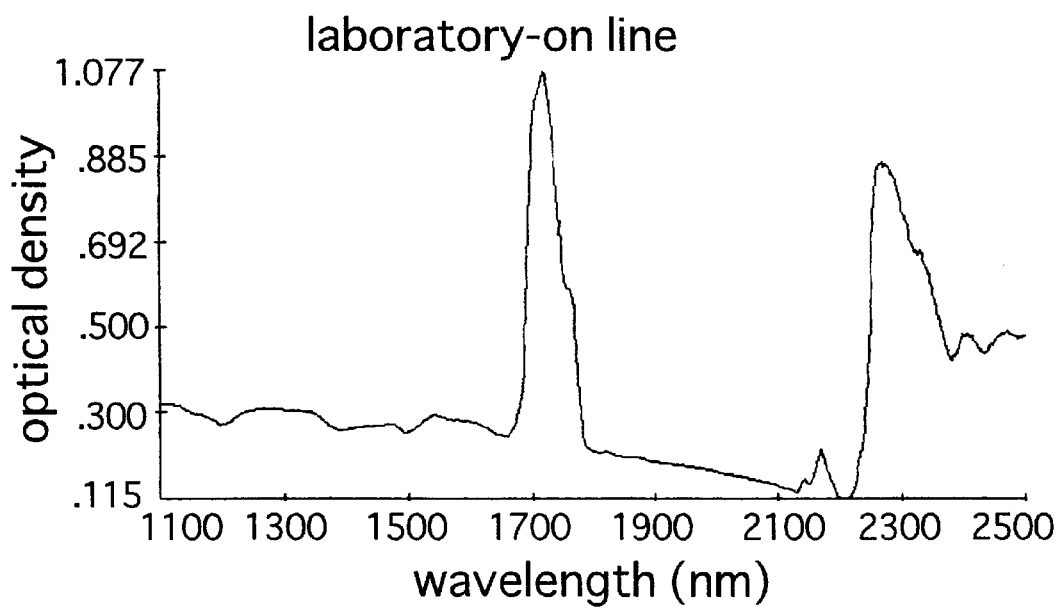
FIG. 2 shows a difference between both the spectra shown in FIG. 1.

FIG. 2 shows a meter difference of data in FIG. 1. The meter difference is obtained by the following equation.

(meter difference)=(spectrum of laboratory analyzer)−(spectrum of on-line analyzer)  (1)

In case of the other regular gasoline sample as well, data showing substantially the same meter difference is obtained, so that the spectrum of the on-line analyzer can be converted into that of the laboratory analyzer by using one sample.

Figure 3:
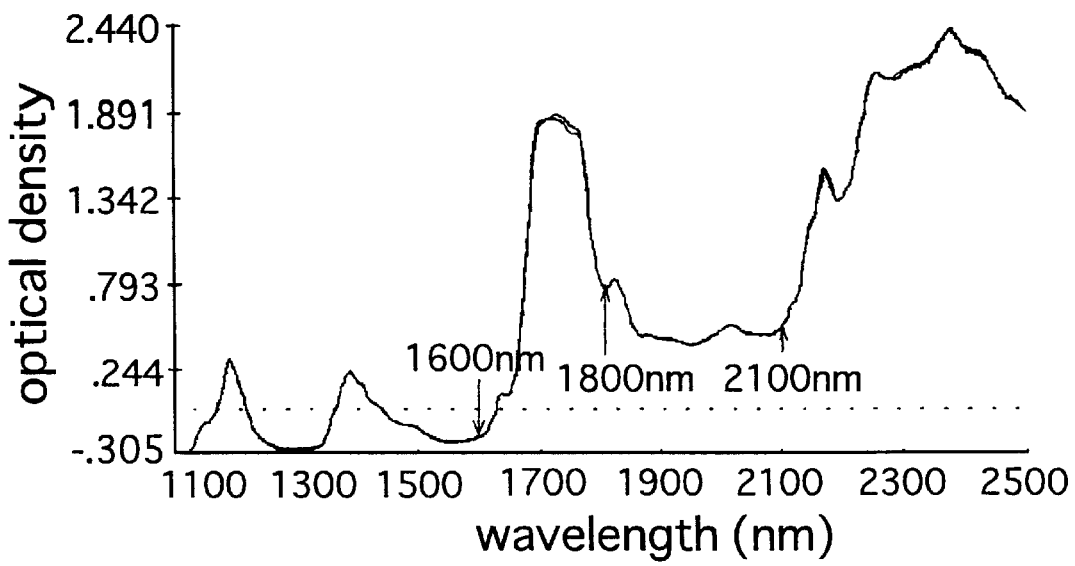
FIG. 3 shows a spectrum obtained by converting the spectrum of the on-line analyzer into the spectrum of the laboratory analyzer by using a meter difference and the spectrum of the laboratory analyzer.

FIG. 3 is a diagram in which the measured spectrum of the on-line analyzer is compared with that of the laboratory analyzer. The same gasoline sample is measured by the on-line analyzer and laboratory analyzer and a conversion spectrum obtained by adding the meter difference to the spectrum obtained by the on-line analyzer is compared with the measured spectrum by the laboratory analyzer. It is understood that both of them are the same spectra in formation wavelength areas (1100 to 1600 nm, 1800 to 2100 nm) of the calibration. Consequently, it is understood that the conversion spectrum can be analyzed by the calibration formed by the laboratory analyzer.

A formation precision of the calibration formed by the laboratory analyzer is shown. As a method for checking the precision, a correlation relation between a hand analyzed value (value which is analyzed by the chemical or physical means) and a measured prediction value (value which is analyzed by the calibration formed by the spectrum measured by the laboratory analyzer and which predicts a characteristic value).

Figure 4:
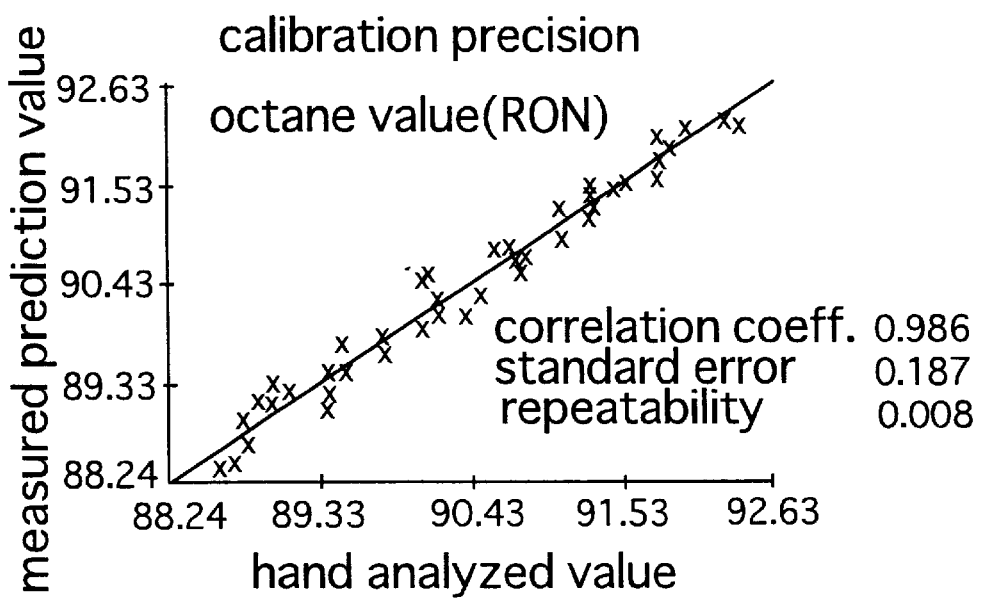
FIG. 4 is a correlation diagram between a hand analyzed value and a measured prediction value of the laboratory analyzer with respect to an octane value of gasoline.
Figure 5:
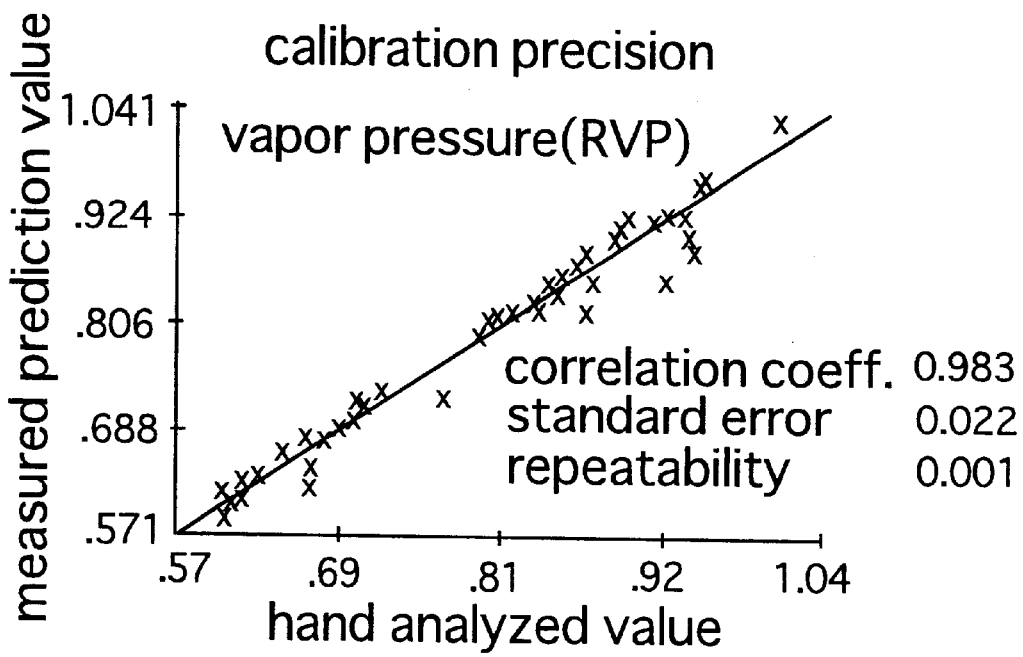
FIG. 5 is a correlation diagram between a hand analyzed value and a measured prediction value of the laboratory analyzer with respect to a vapor pressure of gasoline.
Figure 6:
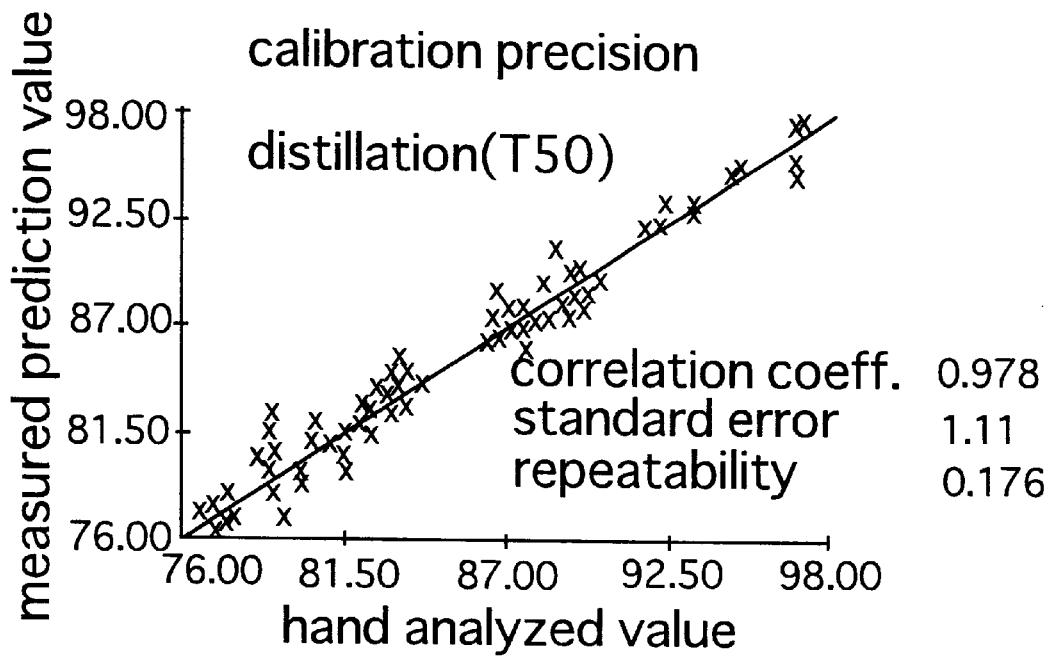
FIG. 6 is a correlation diagram between a hand analyzed value and a measured prediction value of the laboratory analyzer with respect to distillation of gasoline.

FIG. 4 shows a correlation relation between the octane values (RON). An axis of abscissa denotes the octane value as a hand analyzed value and an axis of ordinate shows an octane value as a measured prediction value. The calibration is formed by measuring 60 samples twice for each sample and twice repeatedly in each measurement. FIG. 5 shows a diagram formed by the same method as that in FIG. 4 with respect to the vapor pressure (RVP). FIG. 6 shows a diagram formed by the same method as that in FIG. 4 with respect to the distillation (T50). Each of them shows the fairly good correlation relation.

With respect to the characteristic value of the same sample, the correlation relation between the measured prediction value of the laboratory analyzer and measured prediction value of the on-line analyzer is shown. FIG. 7 shows a correlation relation between the octane values (RON) and an axis of abscissa denotes the octane value of the measured prediction value of the laboratory analyzer and an axis of ordinate denotes the octane value of the measured prediction value of the on-line analyzer. As for the measurement, 30 samples are measured twice. FIG. 8 is a diagram formed by the same method as that in FIG. 7 with respect to the vapor pressure (RVP). FIG. 9 is a diagram formed by the same method as that in FIG. 7 with respect to the distillation (T50). Each of them shows the fairly good correlation relation.

A countermeasure to maintain a measurement precision of the on-line analyzer will now be explained.

1. Countermeasure for a Change in Object to be Measured

When the characteristic value of the composition of the object to be measured at the time of the formation of the calibration is changed, it is measured as abnormal data. When such an object to be measured is correctly measured, the sample is chemically analyzed or analyzed by a physical means to obtain a hand analyzed value and the spectrum is measured by the laboratory analyzer, those data are added, thereby again forming the calibration. The new calibration is transferred to the on-line analyzer. In this manner, in the on-line analyzer, the object to be measured having the new characteristic value can be measured by changing software alone.

2. Countermeasure to Periodically Maintain the On-line Analyzer

The aging change of the on-line analyzer appears in the spectrum. Spectra of the same object to be measured are periodically obtained by the on-line analyzer and laboratory analyzer, the meter difference as a difference between them is obtained, and such a new meter difference is compared with the meter difference which is used at present. When a difference between both of them exceeds a predetermined allowable value, the subsequent measurement is performed by using the new meter difference. Consequently, the on-line analyzer can be periodically maintained.

3. One Laboratory Analyzer Capable of Coping With a Plurality of On-line Analyzers In a petroleum refining factory, a product is not limited to gasoline and there are many objects to be measured, such as gas oil, lamp oil, fuel oil, kerosene, and the like. Although there are many objects which are desired to be analyzed in the on-line manner, it requires an economically large burden to prepare the laboratory analyzer per object. According to the invention, it is unnecessary to make the laboratory analyzer correspond to the on-line analyzer in a one-to-one corresponding manner. The calibration formed by one laboratory analyzer can be transferred to a plurality of on-line analyzers and each meter difference can be obtained between each on-line analyzer and one laboratory analyzer.

Although the above-mentioned description is made in the case where gasoline is set as an object to be measured, the present invention can be applied to a manufacturing line of the other liquid or a material such as gas, solid, or granular object to which the near infrared spectroscopy can be applied.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. A method for analyzing a measured value by an on-line spectral analyzer, comprising the steps of: analyzing an object to be measured, by a chemical means or a physical means to make its characteristic value clear; obtaining a spectrum of the same object to be measured, by an off-line near infrared spectral analyzer; obtaining a calibration indicative of a relation between said spectrum and said characteristic value; selecting at least one sample from among the same kind of objects to be measured; obtaining spectra by said off-line near infrared spectral analyzer and an on-line near infrared spectral analyzer; obtaining a difference between both of the obtained spectra; measuring a spectrum of the same kind of object to be measured, by said on-line near infrared spectral analyzer; correcting the measured spectrum by said difference between both of the spectra; and estimating a characteristic value of the object to be measured, by using the corrected spectrum and said calibration.

2. The method according to claim 1, wherein as said one sample, a sample showing a substantially central value in a measurement range which is covered by said calibration is used.

3. The method according to claim 1, wherein when said object to be measured is changed and an estimated error of the characteristic value exceeds an allowable value in said calibration, a sample of the object to be measured is added and is measured by the off-line infrared spectral analyzer, the calibration is corrected, the corrected calibration is transferred to the on-line analyzer, and the characteristic value of the object to be measured is estimated.

4. The method according to claim 1, wherein spectra of the same object to be measured are obtained by said on-line near infrared spectral analyzer and said off-line near infrared spectral analyzer, a difference between both of new obtained spectra is compared with the difference between both the spectra obtained already and, when the difference between both the new spectra is larger, the characteristic value of the object to be measured is estimated by using the difference between both the new spectra.

5. The method according to claim 1, wherein said calibration obtained by said off-line near infrared spectral analyzer is used by a plurality of on-line near infrared spectral analyzers.

* * * * *